United States Patent [19]

O'Donnell

[11] Patent Number: 5,782,810
[45] Date of Patent: Jul. 21, 1998

[54] MULTIPART RADIOPAQUE AND/OR MAGNETICALLY DETECTABLE TUBE CATHETER AND METHOD OF FABRICATION THEREOF

[76] Inventor: Miles C. O'Donnell, 50 Sagamore Dr., Andover, Mass. 01810

[21] Appl. No.: 754,427

[22] Filed: Nov. 22, 1996

Related U.S. Application Data

[60] Provisional application No. 60/007,479 Nov. 22, 1995.
[51] Int. Cl.⁶ ............................................. A61M 25/00
[52] U.S. Cl. ............................................. 604/280; 128/658
[58] Field of Search .................................. 604/264, 280, 604/282; 128/656, 657, 658

[56] References Cited

U.S. PATENT DOCUMENTS

| | | |
|---|---|---|
| 4,063,561 | 12/1977 | McKenna . |
| 4,244,362 | 1/1981 | Anderson . |
| 4,361,152 | 11/1982 | Patel . |
| 4,431,005 | 2/1984 | McCormick ............ 604/280 |
| 4,571,240 | 2/1986 | Samson et al. . |
| 5,045,071 | 9/1991 | McCormick et al. . |
| 5,045,072 | 9/1991 | Castillo et al. . |
| 5,160,559 | 11/1992 | Scovil et al. . |
| 5,203,777 | 4/1993 | Lee ............................ 604/280 |
| 5,256,158 | 10/1993 | Tolkoff et al. ............ 604/280 |

*Primary Examiner*—John D. Yasko
*Attorney, Agent, or Firm*—Low and Low

[57] ABSTRACT

An improved readily fabricated catheter having a detectable marker incorporated therein wherein the catheter is a conventional flexible and transparent polymeric tube of any usual or desired length, but wherein one end of which is relieved to define a socket or counterbore of an internal diameter somewhat greater than the normal fluid flow bore of the tubing. The catheter further includes a shorter length of tubing having at one end a usual angled or cut face, and having at its other end a short neck of reduced diameter carrying thereon a detectable metallic, magnetic, or radiopaque marker element. The two components are easily telescoped together over their relatively short lengths to confine the marker between the inside and outside walls of the tubing, and the telescoped portions are sealed together to prevent fluid flow or leakage therethrough.

13 Claims, 1 Drawing Sheet

MULTIPART RADIOPAQUE AND/OR MAGNETICALLY DETECTABLE TUBE CATHETER AND METHOD OF FABRICATION THEREOF

CROSS-REFERENCE TO RELATED APPLICATION

This application is based upon Provisional Application Ser. No. 60/007.479, filed Nov. 22, 1995.

BACKGROUND OF THE INVENTION

Hitherto, multipart catheter tubes for tracheal use or other uses as urinary catheters and the like, and having means for radiopaque or magnetic detection thereof have been of relatively complicated construction and have been assembled in diverse manners frequently requiring complex fabrication techniques, extended assembly length of time requirements, including high frequency usage as in RF bonding of tube elements, stretch and shrink fitting of components, and the like.

Typical known catheters of this type for tracheal and like use and diverse fabrication techniques therefor are shown by illustrative U.S. Patents to:

| 4,063,561 | McKenna | Dec. 20, 1977 |
| 4,244,362 | Anderson | Jan. 15, 1981 |
| 4,361,152 | Patel | Nov. 30, 1982 |
| 4,431,005 | McCormick | Feb. 18, 1984 |
| 4,571,240 | Samson et al | Feb. 18, 1986 |
| 5,045,071 | McCormick et al | Sep. 3, 1991 |
| 5,045,072 | Castillo et al | Sep. 3, 1991 |
| 5,160,559 | Scovill et al | Nov. 3, 1992 |
| 5,203,777 | Lee | Apr. 29, 1993 |
| 5,256,158 | Tolkoff et al | Oct. 26, 1993 |

SUMMARY OF THE INVENTION

The present invention provides a unique multipart endotracheal and like tube catheter having a detectable marker therein and which is of ready fabrication, reliable service, and minimum cost.

The same is characterized by ease and speed of assembly, safety in use, and a minimum of components to achieve the final product.

The catheter embraces a conventional flexible and transparent polymeric tube of any usual or desired length, one end of which is relieved to define a socket or counterbore of an internal diameter somewhat greater than the normal fluid flow bore of the tubing. To the socketed end of the tubing length is assembled a short length of tubing having at one end the usual angled face or cut face, and having at its other end a short neck of reduced diameter carrying thereon a detectable metallic, magnetic, or radiopaque marker element, as a ring. The marker is preferably midway or centered along the neck portion. The neck portion outside diameter is substantially equal to the inside diameter of the receiving socket portion.

On assembly, the neck carrying the radiopaque ring is inserted into the socket of the greater tubing length, and the elements fixedly and permanently secured together as by adhesive extending between the neck and socket, or by heat fusion. In so doing, the radiopaque ring is sealed within the now connected tubing and is prevented from any possible contact with the tissue of the body receiving the catheter.

When inserted into the body, the location of the radiopaque ring thereof and thereby the end of the catheter closely adjacent thereto may be readily and quickly determined in usual manner.

BRIEF DESCRIPTION OF THE DRAWINGS

The invention will be better understood with reference to the accompanying drawings, in which.

DETAILED DESCRIPTION OF THE PREFERRED EMBODIMENT

Figure 1:
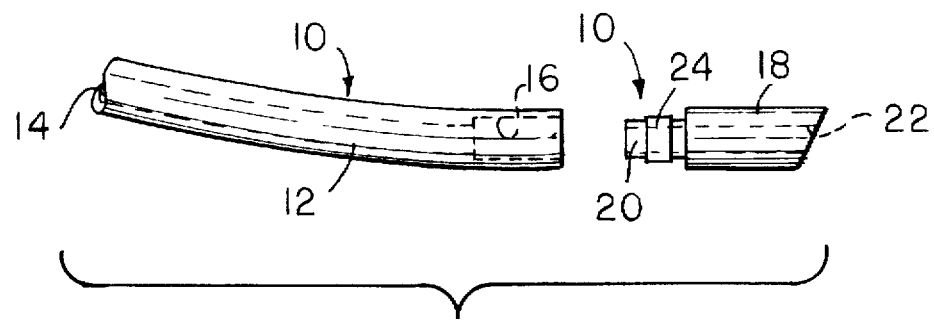
FIG. 1 is a side elevation of the two components of the catheter in unassembled relation, and partially fragmentary.

With reference to the accompanying drawings, the unique catheter of the invention is shown at 10 in exploded and unassembled form in FIG. 1, and includes a major tubing portion 12 of any desired length having a bore 14 for fluid flow, and wherein a coupling end thereof is shown at the right. The tubing length 12 is molded or counterbored at 16 to provide an enlarged inner diameter thereat defining an open socket communicating with the tubing bore 14.

There is provided a shorter tubing length or tip 18 which has a like bore 22 therein and wherein the end face thereof if desired may be slanted or angularly cut in usual manner as illustrated.

Figure 2:
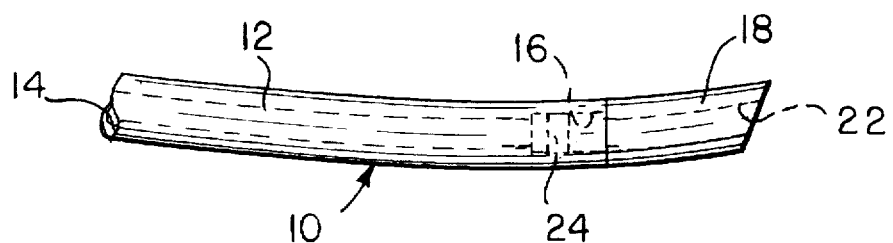
FIG. 2 is similar to FIG. 1, but with the tube sections connected together; and, FIG. 3 is an enlarged fragmentary sectional side elevation of the joined tube lengths showing the positioning of the radiopaque ring.

Tubing length 18 at its other end is provided with a reduced diameter neck-like portion 20 surrounding bore 22 and of a length substantially corresponding to that of socket 16 in tubing 12. Reduced portion 20 is sized to have a close and snug sliding fit on initial insertion into socket 16, as is seen in FIG. 2.

The reduced portion 20 carries therearound a marker band 24 of metal or other materials well known in the art. Such bands may be of radiopaque material or magnetically detectable, as a ferrous metal ring, for example, as is commonly practiced. If a marker 24 is a band or annulus, the same may be initially snugly slid and fitted onto the neck 20. The marker 24 may comprise a metal-deposited layer or coating on tube portion 20 or therearound.

The prior art, as the patents to McCormick U.S. Pat. Nos. 5,045,071 or Pat. No. 4,431,005 or Samson et al U.S. Pat. No. 4,571,240 are generally illustrative of such marker bands, for example.

Heretofore, it has been considered necessary and customary to fully telescopingly interfit tubing members along their entire lengths, as illustratively in the McCormick or Samson patents. Such full length assemblage is difficult to achieve in a reliable and expeditious manner, as well as entailing substantial fabrication costs.

For example, the prior art as Samson requires substantially complex stretching and shrinking operations over nearly the full length of the tubing members to assemble the same.

In the present invention, as is evident from the drawings, the primary tubing element 12 having lengths comparable to those shown in McCormick U.S. Pat. No. 4,431,005, for example, is unaltered throughout its length, except for the relatively short socketed end 16 thereof. Such a socket is preferably less than one inch in length.

Figure 3:
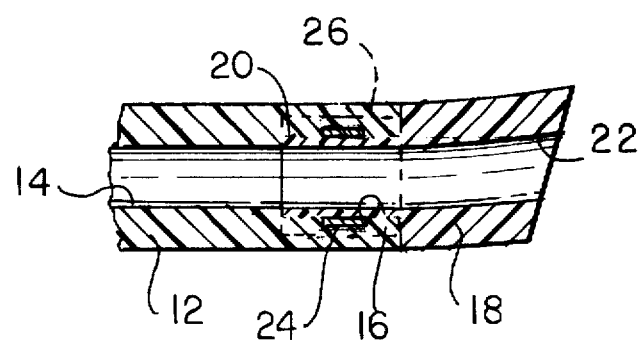

Upon assembly of the tube end 18 to tubing 12 by insertion of neck portion 20 into socket 16, the two telescoping elements 16, 20 are then bonded together as by an adhesive compatible with the plastic tubing, by heat fusing of the polymeric tubing, or by an organic solvent compatible with the polymeric material. In any mode of assembly, the tubing lengths become fused and integral along their initial contacting surfaces as shown at 26 in FIG. 3.

In the case of an adhesive or liquid solvent, the same is coated onto the reduced length 20 and preferably also applied within the socket 16 prior to telescoping assembly of the short interfitting lengths. In the case of heat fusion of the joint, suitable radiant or induction heat is applied in known manner circumferentially of the telescoped portions so as to melt the tubes together thereat.

It will be seen on the interfitting of tube end 18 into tubing 12 that the marker as metal or like band 24 will be fully enclosed and effectively encapsulated within the now integral tubing lengths 12 and 18 between the inside bore wall and the exterior wall of the overall tubing, whereby no metallic or other marker material portion has any physical contact with the tissues of a patient during use or treatment. Further, as the tubes are now integral, there is no likelihood of leakage through the initially interfitted joint in either direction from or to the patient.

As a consequence, the device and technique of the present invention constitutes a substantial improvement over the prior art and contribution to medical science.

In the preferred embodiment it will be seen that the greater tubing length 12 is provided with the socket 16 and the shorter length 18 has the reduced neck 20. If desired, the socket 16 may be provided on the shorted tubing length 18 and the reduced neck on the longer tubing length 12.

While I have described a preferred embodiment of my invention, it is to be understood that other variations and modifications thereof are contemplated and embraced by the scope of the following claims.

What I claim is:

1. An improved catheter having a detectable marker therein comprising,
   a length of flexible polymeric tubing defining a bore of generally uniform diameter, said tubing defining a first length having a socket at one end of greater diameter than said bore and surrounded by an annular wall having an inside surface and defining a second length having a neck of reduced diameter having an outside surface substantially corresponding to the diameter of said socket,
   a marker incorporated into said tubing and disposed between said socket and neck surfaces, and,
   means sealing said marker within said tubing to preclude access of body or external fluids thereto.

2. The improved catheter of claim 1 wherein said marker is a radiopaque annulus.

3. The improved catheter of claim 1 wherein said marker is of magnetically detectable material.

4. The improved catheter of claim 2 wherein said marker is initially carried on said neck.

5. The improved catheter of Claim 1 wherein said tubing socket and said tubing neck are integrally bonded together between their inside and outside surfaces to surround said marker.

6. The improved catheter of claim 5 wherein said bonding is effected by adhesive disposed between said tubing socket and said tubing neck.

7. The improved catheter of claim 5 wherein said bonding is effected by the presence of a solvent for said tubing between said socket and said tube neck.

8. The improved catheter of claim 5 wherein said bonding is effected by a heat fused joint between said tubing socket and said tubing neck.

9. The improved catheter of claim 5 wherein said second tubing length is substantially shorter than said first tubing length.

10. The improved catheter of claim 5 wherein said socket has depth on the order of one inch.

11. An improved catheter having a detectable marker therein comprising,
    a first tubing length having a socket therein of relatively short depth and of greater inside surface diameter than the bore of said tubing length,
    a second tubing length having a reduced diameter neck at one end thereof of a length substantially corresponding to the depth of said socket and of an outside surface diameter substantially corresponding to the inside diameter of said socket,
    a detectable marker carried by said neck,
    said neck and said socket being telescoped together thereby to seat said neck in said socket and dispose said marker between the tubing bore and the external wall surface of said tubing lengths, and,
    means for integrally joining said neck and said socket thereby to seal said detectable marker within said tubing.

12. The improved catheter of claim 11 wherein said tubing length having said neck thereon is of substantially shorter overall length than said tubing length having said socket therein.

13. The improved catheter of claim 11 wherein said marker is an annular member.

* * * * *